(12) United States Patent
Copland et al.

(10) Patent No.: US 10,485,417 B2
(45) Date of Patent: Nov. 26, 2019

(54) OPTICAL MEASUREMENT SYSTEM AND METHOD WITH TARGET BRIGHTNESS LEVEL ADJUSTMENT

(71) Applicant: AMO WAVEFRONT SCIENCES, LLC, Santa Ana, CA (US)

(72) Inventors: Richard J. Copland, Albuquerque, NM (US); David J. Tanzer, San Diego, CA (US); Thomas D. Raymond, Edgewood, NM (US)

(73) Assignee: AMO WaveFront Sciences, LLC, Santa Clara, CA (US)

( * ) Notice: Subject to any disclaimer, the term of this patent is extended or adjusted under 35 U.S.C. 154(b) by 152 days.

(21) Appl. No.: 15/701,326

(22) Filed: Sep. 11, 2017

(65) Prior Publication Data

US 2017/0367572 A1 Dec. 28, 2017

Related U.S. Application Data

(63) Continuation of application No. 14/791,175, filed on Jul. 2, 2015, now Pat. No. 9,757,025.
(Continued)

(51) Int. Cl.
A61B 3/00 (2006.01)
A61B 3/103 (2006.01)
A61B 3/11 (2006.01)

(52) U.S. Cl.
CPC .......... *A61B 3/0091* (2013.01); *A61B 3/0025* (2013.01); *A61B 3/0075* (2013.01);
(Continued)

(58) Field of Classification Search
CPC ....... A61B 3/14; A61B 3/0008; A61B 3/0075; A61B 3/112
(Continued)

(56) References Cited

U.S. PATENT DOCUMENTS 4,927,259 A 5/1990 Weber
5,036,347 A 7/1991 Tsunekawa et al.
(Continued)

FOREIGN PATENT DOCUMENTS

CN 102283633 A 12/2011
EP 2422691 A1 2/2012
(Continued)

OTHER PUBLICATIONS

European Search Report for Application No. EP17188112, dated Dec. 18, 2017, 7 pages.
(Continued)

*Primary Examiner* — Hung X Dang
(74) *Attorney, Agent, or Firm* — Johnson & Johnson Surgical Vision, Inc.

(57) ABSTRACT

A system and method for measuring a characteristic of an eye of a subject receive data pertaining to the subject; assign the subject to an assigned age category based on the data pertaining to the subject; adjust a brightness level of a fixation target according to the assigned age category for the subject; provide the fixation target for a subject to view; and objectively measure at least one characteristic of the eye of the subject while the subject views the fixation target at the adjusted brightness level.

16 Claims, 9 Drawing Sheets

Related U.S. Application Data

(60) Provisional application No. 62/020,515, filed on Jul. 3, 2014.

(52) U.S. Cl.
CPC ............ *A61B 3/103* (2013.01); *A61B 3/1035* (2013.01); *A61B 3/112* (2013.01)

(58) Field of Classification Search
USPC ........ 351/224, 239, 243, 226, 222, 240, 200
See application file for complete search history.

(56) References Cited

U.S. PATENT DOCUMENTS

| | | | |
|---|---|---|---|
| 5,777,719 A | 7/1998 | Williams et al. | |
| 6,550,917 B1 | 4/2003 | Neal et al. | |
| 7,976,163 B2 | 7/2011 | Campbell et al. | |
| 8,016,420 B2 | 9/2011 | Yee et al. | |
| 8,384,002 B2* | 2/2013 | Holladay | A61F 2/1618 250/201.2 |
| 8,833,940 B2 | 9/2014 | Yee et al. | |
| 9,066,796 B2 | 6/2015 | Holladay | |
| 2009/0032679 A1 | 2/2009 | Holladay | |
| 2010/0280405 A1 | 11/2010 | Musialik et al. | |
| 2011/0149239 A1 | 6/2011 | Neal et al. | |

FOREIGN PATENT DOCUMENTS

| | | |
|---|---|---|
| WO | 2010113193 A1 | 10/2010 |
| WO | 2013059656 A2 | 4/2013 |

OTHER PUBLICATIONS

International Search Report and Written Opinion for Application No. PCT/US2015/039132, dated Nov. 20, 2015, 13 pages.

* cited by examiner

US 10,485,417 B2

OPTICAL MEASUREMENT SYSTEM AND METHOD WITH TARGET BRIGHTNESS LEVEL ADJUSTMENT

CROSS-REFERENCE TO RELATED APPLICATION

This application is a continuation of, and claims the priority benefit under 35 U.S.C. 4 120 from U.S. patent application Ser. No. 14/791,175, filed on 2 Jul. 2015 in the names of Richard J. Copland, et al., now U.S. Pat. No. 9,757,025, which is a non-provisional of and claims priority to U.S. Provisional Application No. 62/020,515 filed on Jul. 3, 2014, which are hereby incorporated by reference in theft entirety.

FIELD OF INVENTION

Embodiments of this invention generally pertain to the field of vision diagnostics, and particularly to a method and system for objectively measuring an optical characteristic of an eye.

BACKGROUND

Ocular aberrations typically produce unwanted results in the form of bad eyesight. To be adequately treatable, these aberrations need to be measured and characterized. To this end, various devices, apparatuses, and methods have been developed for objectively measuring characteristics, including aberrations, of a subject's eye. The measured characteristics of the eye may be employed for planning corrective actions, including for example ocular surgery such as Laser-Assisted in situ Keratomileusis ("LASIK"), laser cataract surgery, and various other treatments.

LASIK and other eye surgeries are typically planned based on the far point refractive characteristics of the eye. So it is important that an optical measurement system ensures that the subject's eye is drawn to its farthest possible refractive state when making measurements for planning the surgery.

Furthermore, when eye surgery is being planned, it is desired to measure the eye when the pupil has a large diameter so that the optical characteristics of the eye can be measured over a large area of the eye. This not only affects the treatment planning, but is also important in disqualifying a subject from being a candidate for eye surgery if certain optical abnormalities are found in the wavefront map of the eye. Such irregularities can be an indication of keratoconus or other problems. For this reason, many equipment manufacturers disqualify a subject from eye surgery if the pupil diameter is less than some minimum threshold diameter (e.g., 5 mm).

However, there are some problems in simultaneously insuring that the subject's eye is drawn to its farthest possible refractive state when making measurements, while also maintaining the pupil open with as large of a diameter as possible.

To meet the requirement that that insure that the subject's eye should be drawn to its farthest possible refractive state when making measurements, many optical measurement systems employ an internal visible target for the subject to look at or follow while the measurements are made, and the target is intended to draw the eye to its farthest possible refractive state. If this target is too bright, then the pupil will close and become smaller. Hence, it is desired to make the target as dim as possible. This is especially the case with older people, who often have a habitually small pupil. Thus, a dimmer target can open an older person's pupil to be wider.

On the other hand, however, if the target is too dim, then for some younger people, the eye might not follow the target and reach its farthest possible refractive state. In this case, it is said that the eye is "accommodated." This occurs because young people are capable of changing the refractive state of their eyes to focus at near or far distances, which in general is not the case for older people. It has been observed clinically that, for a younger person whose eye is capable of accommodation, increasing the brightness level of the target will increase the likelihood of ensuring that optical measurements are made with the eye in its farthest possible refractive state.

To address these conflicting requirements, many optical measurement systems employ a target whose brightness level is an attempted compromise between being too bright for older subjects, and too dim for younger subjects. However, in practice, there seems to be no single target brightness level that achieves a satisfactory compromise.

SUMMARY OF THE INVENTION

Therefore, it would be desirable to provide a system and method for making objective measurements of a subject's eye which can draw the eye into its farthest possible refractive state while measurements are made while also maintaining a large pupil size so as to obviate one or more problems due to limitations and disadvantages of the related art. In particular, it would be desirable to provide a system and method for making objective measurements of a subject's eye which can accomplish these objectives for younger subjects as well older subjects.

In one aspect of the invention, a method is provided for measuring at least one characteristic of an eye of a subject. The method comprises: receiving data pertaining to the subject; assigning the subject to an assigned age category based on the data pertaining to the subject; adjusting a brightness level of a fixation target to a selected brightness level corresponding to the assigned age category for the subject; providing the fixation target for a subject to view; and objectively measuring the at least one characteristic of the eye of the subject while the subject views the fixation target at the selected brightness level.

In some embodiments, the method further comprises assigning the subject to a first age category when the data pertaining to the subject indicates that the subject is younger than a threshold age; and assigning the subject to a second age category when the data pertaining to the subject indicates that the subject is older than the threshold age.

In some versions of these embodiments, the method further comprises: adjusting the brightness level of the fixation target to have a first value when the subject is assigned to the first age category; and adjusting the brightness level of the fixation target to have a second value when the subject is assigned to the second age category, where the first value is greater than the second value.

In some versions of these embodiments, the first value is approximately 2.0 cd/m$^2$ and the second value is 0.5 cd/m$^2$.

In some versions of these embodiments, the threshold age is between 40 and 43 years old.

In some embodiments, the method further comprises: assigning the subject to a first age category when the data pertaining to the subject indicates that the subject is younger than a first threshold age; assigning the subject to a second age category when the data pertaining to the subject indicates that the subject is older than the first threshold age but younger than a second threshold age; and assigning the subject to a third age category when the data pertaining to the subject indicates that the subject is older than the second threshold age.

In some versions of these embodiments, the method further comprises: adjusting the brightness level of the fixation target to have a first value when the subject is assigned to the first age category; adjusting the brightness level of the fixation target to have a second value when the subject is assigned to the second age category; and adjusting the brightness level of the fixation target to have a third value when the subject is assigned to the third age category, wherein the first value is greater than the second value, and the second value is greater than the third value.

In some versions of these embodiments, the first threshold age is approximately 30 years old, and the second threshold age is approximately 43 years old.

In some embodiments, the method further comprises: determining at least one vision parameter of the subject; and adjusting a brightness level of the fixation target according to the determined vision parameter of the subject, wherein the determined vision parameter is one of a level of myopia of the eye and a level of astigmatism of the eye.

In some embodiments, the method further comprises: detecting an ambient illumination level in a vicinity of the optical measurement system; and adjusting the brightness level of the fixation target in response to the indicated ambient illumination level.

In another aspect of the invention, a system comprises: an optical measurement instrument configured for objectively measuring at least one characteristic of an eye of a subject; a fixation target configured for a subject to view while the optical measurement instrument objectively measures the at least one characteristic of the eye; an input configured to receive data pertaining to the subject; and one or more processors. The one or more processors are configured to receive the data pertaining to the subject; to assign the subject to an assigned age category based on the data pertaining to the subject, and to adjust a brightness level of a fixation target to a selected brightness level corresponding to the assigned age category for the subject while the optical measurement instrument objectively measures the at least one characteristic of the eye.

In some embodiments, the one or more processors is/are configured to assign the subject to a first age category when the data pertaining to the subject indicates that the subject is younger than a threshold age, and to assign the subject to a second age category when the data pertaining to the subject indicates that the subject is older than the threshold age.

In some versions of these embodiments, the one or more processors is/are configured to adjust the brightness level of the fixation target to have a first value when the subject is assigned to the first age category, and to adjust the brightness level of the fixation target to have a second value when the subject is assigned to the second age category, where the first value is greater than the second value.

In some versions of these embodiments, the first value is approximately 2.0 cd/m$^2$ and the second value is 0.5 cd/m$^2$.

In some versions of these embodiments, the threshold age is between 40 and 43 years old.

In some embodiments, the one or more processors is/are configured to assign the subject to a first age category when the data pertaining to the subject indicates that the subject is younger than a first threshold age, and to assign the subject to a second age category when the data pertaining to the subject indicates that the subject is older than the first threshold age but younger than a second threshold age, and to assign the subject to a third age category when the data pertaining to the subject indicates that the subject is older than the second threshold age.

In some versions of these embodiments, the one or more processors is/are configured to adjust the brightness level of the fixation target to have a first value when the subject is assigned to the first age category, to adjust the brightness level of the fixation target to have a second value when the subject is assigned to the second age category, and to adjust the brightness level of the fixation target to have a third value when the subject is assigned to the third age category, wherein the first value is greater than the second value, and the second value is greater than the third value.

In some versions of these embodiments, the first threshold age is approximately 30 years old, and the second threshold age is approximately 43 years old.

In some embodiments, the one or more processors is/are configured to determine at least one vision parameter of the subject, and to adjust a brightness level of the fixation target according to the determined vision parameter of the subject, wherein the determined vision parameter is one of a level of myopia and a level of astigmatism of the eye.

In some embodiments, the one or more processors is/are configured to receive an indication of an ambient illumination level in a vicinity of the system, and is/are further configured to adjust the brightness level of the fixation target in response to the indicated ambient illumination level.

In yet another aspect of the invention, a method is provided for measuring a characteristic of an eye of a subject. The method comprises: providing a fixation target for a subject to view; ascertaining a diameter of a pupil of the eye of the subject while the subject views the fixation target; adjusting a brightness level of the fixation target to a selected brightness level corresponding to the ascertained diameter of the pupil of the eye; and objectively measuring at least one characteristic of the eye of the subject while the subject views the fixation target at the selected brightness level.

In still another aspect of the invention, a system comprises: an optical measurement instrument configured for objectively measuring at least one characteristic of an eye of a subject; a fixation target configured for a subject to view while the optical measurement instrument objectively measures the at least one characteristic of the eye; and one or more processors. The one or more processors are configured to ascertain a diameter of a pupil of the eye of the subject, and to cause a brightness level of the fixation target to be adjusted according to the ascertained diameter of the eye while the optical measurement instrument objectively measures the at least one characteristic of the eye.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by referring to the following detailed description

DETAILED DESCRIPTION

As discussed above, it would be desirable to provide an optical measurement system and method of operation of an optical measurement system which can draw the eye into its farthest possible refractive state when measurements are made, while also maintaining a large pupil size, for both younger subjects and older subjects. The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Figure 1:
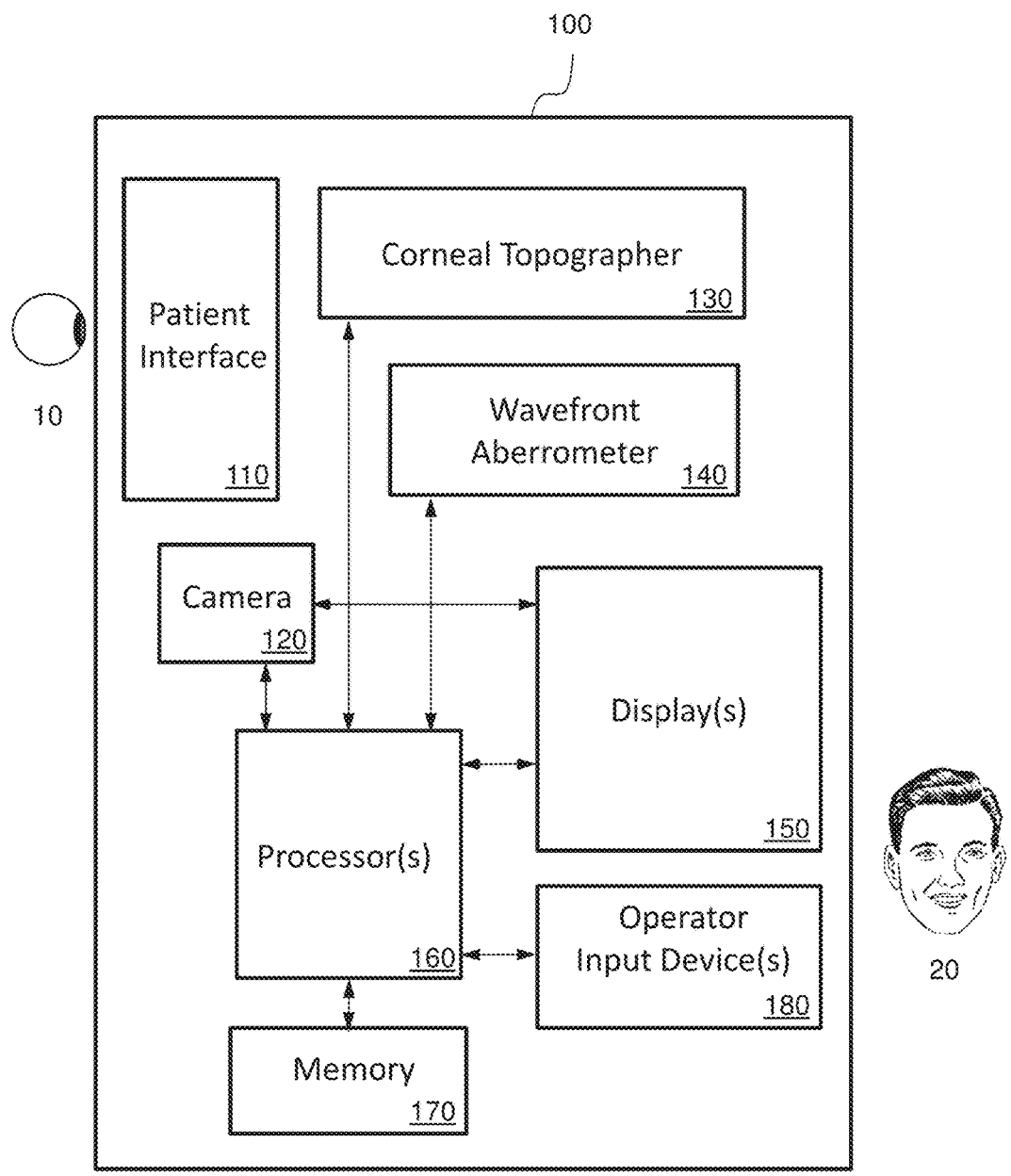
FIG. 1 is a functional block diagram of one embodiment of an optical measurement system.

FIG. 1 is a functional block diagram of one embodiment of an optical measurement instrument or optical measurement system 100 for measuring one or more characteristics of an eye 10. Optical measurement system 100 includes a patient interface (e.g., a headrest and eye examination area), a camera 120, a corneal topographer 130, a wavefront aberrometer 140, one or more displays 150, one or more processors 160 and associated storage (e.g., memory) 170, and one or more operator input devices 180 for receiving input or instructions from an operator 20. It should be understood that optical measurement system 100 is simply one embodiment for illustrating principles of the invention, and that many variations are possible which may omit certain elements, add additional elements, and/or change some of the elements. For example, another optical measurement system incorporating one or more aspects of this invention may omit corneal topographer 130. Some implementations may include additional elements, for example one or more loudspeakers.

In some implementations, camera 120 may be an eye alignment camera which is used to insure proper eye alignment when making corneal topography and/or wavefront aberrometry measurements with corneal topographer 130 and/or wavefront aberrometer 140. Beneficially, camera 120 alone or in conjunction with processor(s) 160 may provide a continuous live display of eye 10 to operator 20 via display 150.

Wavefront aberrometer 140 may measure wavefront aberrations of eye 10 from which one or more optical characteristics may be ascertained. As described in greater detail below with respect to FIG. 2, wavefront aberrometer 140 includes a fixation target for the subject to view when measurements are made of eye 10.

Although example configurations of corneal topographer 130 and wavefront aberrometer 140 will be described in further detail below with respect to FIG. 2, it should be understood that these elements may employ any of a variety of other configurations.

Display(s) 150 may include one or more display devices which provide images and/or data to operator 20 under control of processor(s) 160. Such images and data may include operating instructions and/or requests for input from operator 20, images of eye 20 produced by camera 120, images and data reflecting measurements of eye 10 performed by corneal topographer 130 and/or wavefront aberrometer 140, etc. Display(s) 150 may include one or more flat panel displays, including one or more touchscreens, individual lights (e.g., light emitting diodes), or any other convenient display device(s).

Processor(s) 160 execute(s) computer-readable instructions for performing operations of optical measurement system 100. Such operations may include adjusting one or more operating parameters of corneal topographer 130 and/or wavefront aberrometer 140, processing data output by corneal topographer 130 and/or wavefront aberrometer 140, interpreting and responding to inputs and/or instructions received by operator input device(s) 180, generating images and/or data for display by display(s) 150, etc. In particular, as described in greater detail below, processor(s) 160 may control or adjust a brightness level of a fixation target employed by optical measurement system 100, for example as part of wavefront aberrometer 140. Processor(s) 160 may perform into operations using instructions and/or data stored in associated storage 170. Storage 170 may include any combination of volatile memory devices (e.g., random access memory), nonvolatile memory devices (e.g., read only memory, FLASH memory), computer readable media such as hard disk drives, optical disks, etc. In particular, storage 170 may store an operating system for processor(s) 160 and one or more computer programs which are executed by processor(s) 160 during operation of optical measurement system 100. In some implementations, storage 170 may store computer-readable instructions which cause processor(s) 160 to execute one or more algorithms for adjusting or controlling an illumination level of a fixation target employed by optical measurement system 100 used when making wavefront measurements of a subject's eye 10. In some implementations, storage 170 may store computer-readable instructions which cause processor(s) 160 to execute one or more algorithms described below with respect to FIGS. 7-8. In some implementations, storage 170 may store raw data produced by corneal topographer 130 and/or wavefront aberrometer 140, and/or data from corneal topographer 130 and/or wavefront aberrometer 140 which has been processed by processor(s) 160.

Operator input device(s) 180 may include any combination of the following devices: keyboard, touchscreen, touchpad, joystick, pushbuttons, roller ball, mouse, keypad, microphone, etc.

In general, processor(s) 160 operate in conjunction with display(s) 150 and operator input device(s) 180 to provide a user interface for receiving instructions and data from operator 20 and for communicating warnings, instructions, and data to operator 20.

Figure 2:
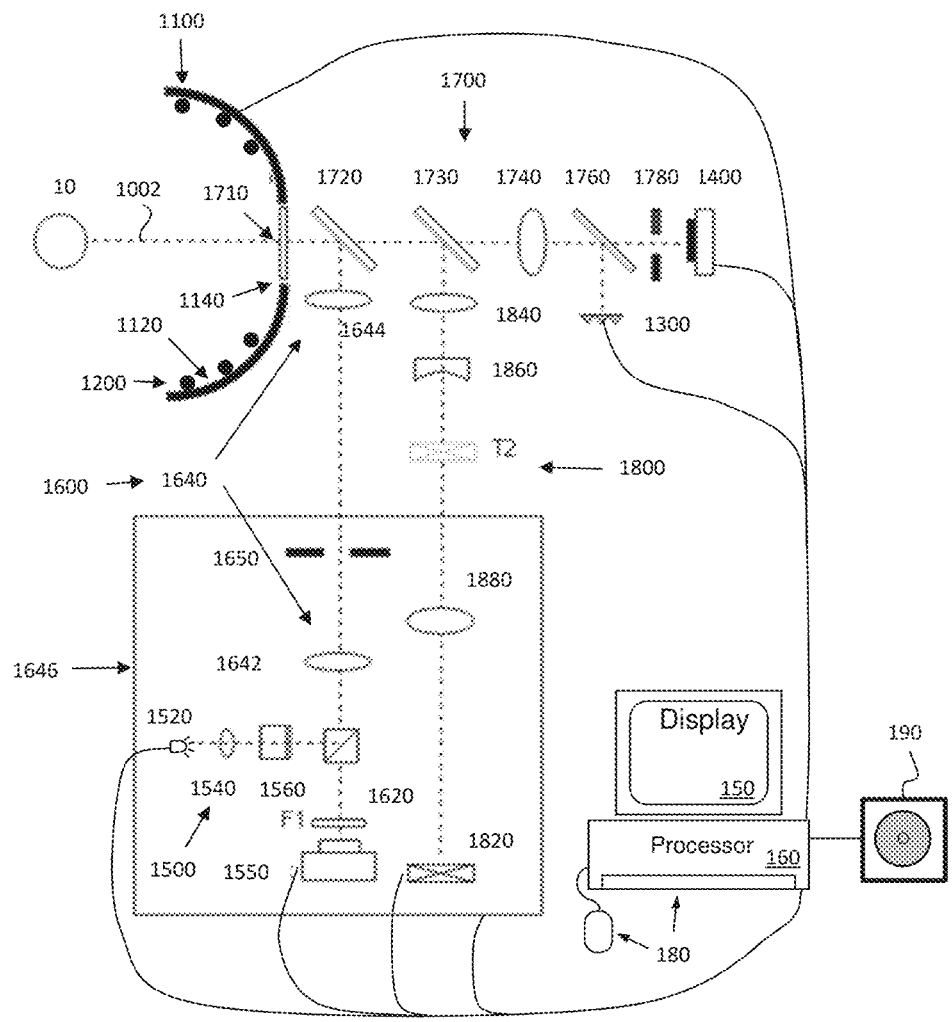
FIG. 2 is a more detailed diagram of portions of one embodiment of an optical measurement system.

FIG. 2 is a more detailed diagram of portions of one embodiment of an optical measurement instrument or optical measurement system 200. System 200 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); a detector array 1400; a display 150; a processor 160; operator input devices 180; a third light source 1500 providing a probe beam; a wavefront sensor 1550; and an optical system 1700 disposed along a central axis 1002 passing through the opening or aperture 1140 of the structure 1100. Optical system 1700 comprises a quarterwave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element. Beneficially, system 200 further comprises a fixation target 1800, comprising one or more light sources 1820 and lenses 1840, 1860, and 1880.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation.

In some embodiments, lamp 1520 of third light source 1500 may be an 840 nm SLD (super luminescent laser diode).

Beneficially, wavefront sensor 1550 may be Shack-Hartmann wavefront sensor comprising a detector array and a plurality of lenslets for focusing received light onto its detector array. In that case, the detector array may be a CCD, a CMOS array, or another electronic photosensitive device. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety. However, other wavefront sensors may be employed instead.

Wavefront sensor 1550 outputs signals to processor(s) 160 which use(s) the signals to determine ocular aberrations of eye 10. Beneficially, processor(s) 160 is/are able to better characterize eye 10 by considering the corneal topography of eye 10, which may also be determined by processor(s) 160 based on outputs of detector array 1400, as explained above.

The configurations and operation of display 150, processor 160, and operator input devices 180 have been described above with respect to FIG. 1 and will not be repeated.

As shown in FIG. 2, optical measurement system 200 further includes a loudspeaker 190 which may provide audible warnings, instructions and/or other audible feedback to operator 20.

Beneficially, system 200 includes fixation target 1800 for the subject to view. Fixation target 1800 is used to control the subject's accommodation, because as mentioned above it is often desired to measure the refraction and wavefront aberrations when eye 10 is focused at its far point (e.g., because LASIK treatments are primarily based on this).

Figure 3:
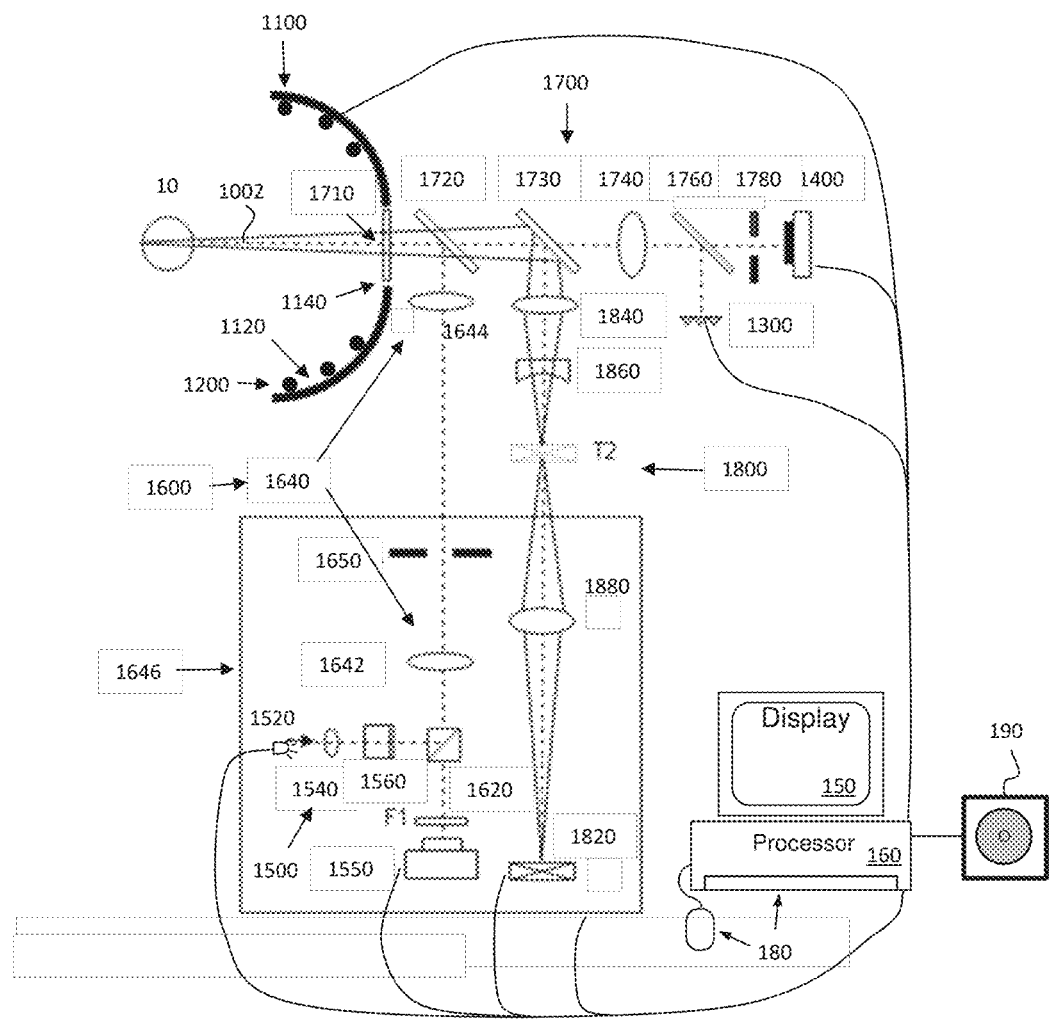
FIG. 3 illustrates rays for a fixation target in the system of FIG. 2.

FIG. 3 illustrates rays for fixation target 1800 in optical measurement system 200.

Light originates from the light source 1820. As shown in FIG. 2, light source 1820 is controlled by one or more signals from processor 160. In particular, processor(s) 160 may turn on, turn off, and control the intensity of light source 1820 and thereby the brightness level of fixation target 1800. In various implementations, this could be a back lit reticule or an LCD microdisplay. Lens 1840 collects the light and forms an aerial image T2 of light source 1820. This aerial image is what the subject actually views. In some embodiments, the aerial image T2 has the pattern and shape of a spoked wheel with a clear center which attracts subjects to stare at it. Rays drawn from T1 to T2 indicate this imaging condition. Lens 1840 may be used to magnify the aerial image T2 to the appropriate size and also to provide mechanical clearance as the movable stage or platform 1646 moves.

FIG. 3 shows the rays from the retina of eye 10 to T2. This indicates a condition when the target T2 would appear in focus to the subject. This state would tend to induce accommodation and would not be desired for measuring the far point of the eye.

From this condition, movable stage or platform 1646 is moved down until eye 10 can no longer focus the target T2 and the target T2 appears fuzzy. This relaxes the subject's accommodation until the far point is reached, at which point the refraction and aberrations of eye 10 are measured.

FIG. 3 shows that the subject views the fixation target T2 through lenses 1860 and 1880. Two lenses are used in order to form a retrofocus lens so that the principal plane of the lens group can be made to coincide with the principal plane of lens 1644 of wavefront analysis system 1600. This makes it so the vergences on the path of wavefront sensor 1550 and the fixation target path match for all positions of movable stage 1646, which is a necessary condition for the fogging function to work properly.

Figure 4:
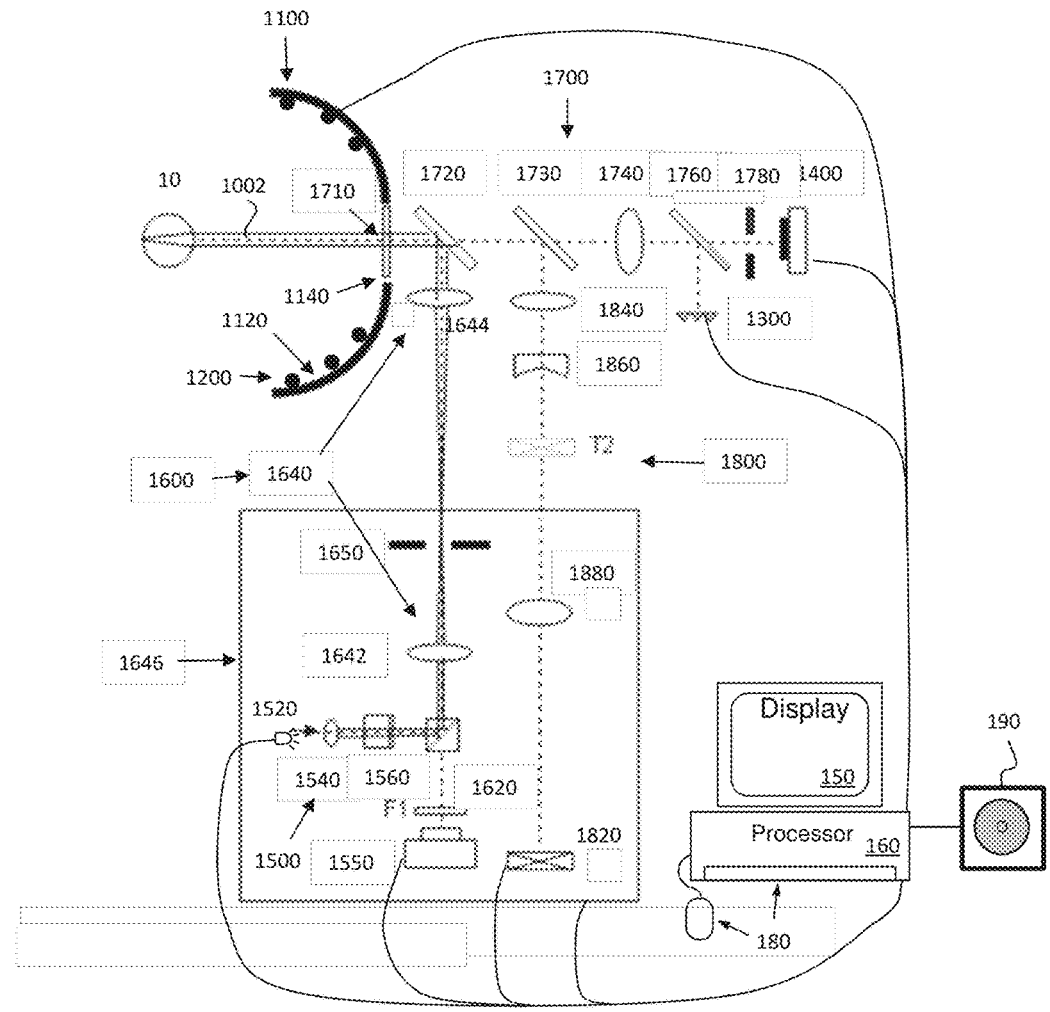
FIG. 4 illustrates rays for a probe beam in the system of FIG. 2.

FIG. 4 illustrates rays for a probe beam employed in system 200 of FIG. 2 for wavefront analysis.

Beneficially, in system 200 the refraction and aberrations of eye 10 are measured using light that is injected into eye 10 and that scatters off the eye's retina.

In FIG. 4 rays leave lamp 1520 and are collimated by lens 1540. The light passes through light source polarizing beam splitter 1560. The light entering light source polarizing beam splitter 1560 is partially polarized. Light source polarizing beam splitter 1560 reflects light having a first, S, polarization, and transmits light having a second, P, polarization so the exiting light is 100% linearly polarized. In this case, S and P refer to polarization directions relative to the hypotenuse in light source polarizing beam splitter 1560.

Light from light source polarizing beam splitter 1560 enters polarizing beamsplitter 1620. The hypotenuse of polarizing beamsplitter 1620 is rotated 90 degrees relative to the hypotenuse of light source polarizing beamsplitter 1560 so the light is now S polarized relative the hypotenuse of polarizing beamsplitter 1620 and therefore the light reflects upwards.

The light from polarizing beamsplitter 1620 travels upward and passes through telescope 1640 comprising lenses 1642 and 1644. Back reflections off of lenses 1642 and 1644 will be S polarized so they will reflect off polarizing beamsplitter 1620 and be directed toward lamp 1520. In the figure, the polarization is perpendicular to the plane of the paper. This reflection prevents back reflections off 1642 and 1644 from reaching wavefront sensor 1550. In practice, the reflectivities of 1642 and 1644 should be less than 0.5% for no back reflections to appear on wavefront sensor 1550.

After passing through lens 1644, the light reflects off first beamsplitter 1720, retaining its S polarization, and then travels through quarterwave plate 1710. Quarterwave plate 1710 converts the light to circular polarization. The light then travels through aperture 1140 in principal surface 1120 of structure 1100 to eye 10. Beneficially, the beam diameter on the cornea is between 1 and 2 mm. Then the light travels through the cornea and focuses onto the retina of eye 10.

The focused spot of light becomes a light source that is used to characterize eye 10 with wavefront sensor 1550.

Figure 5:
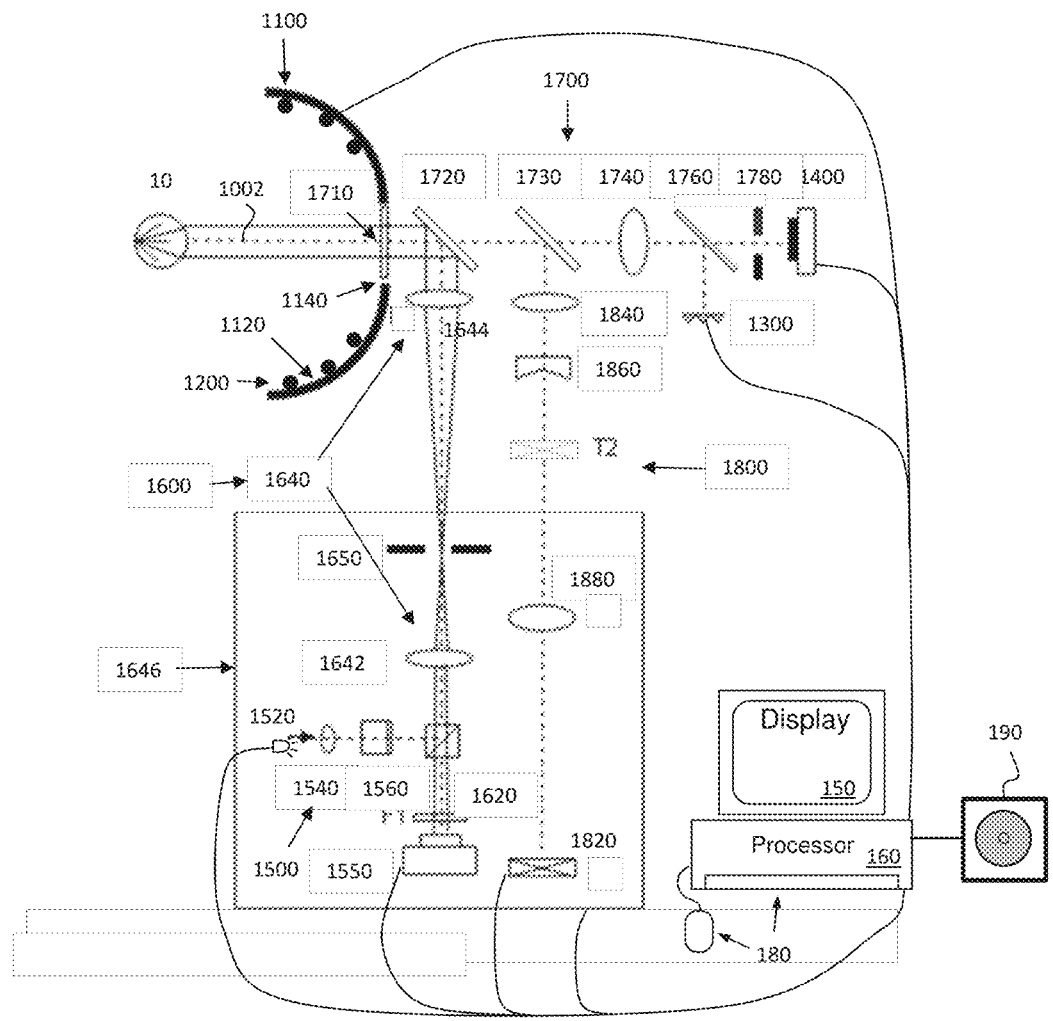
FIG. 5 illustrates rays for a wavefront sensor in the system of FIG. 2.

FIG. 5 illustrates rays from the focused spot on the retina that to the wavefront sensor 1550 in system 200 of FIG. 2.

Light from the probe beam that impinges on the retina of eye 10 scatters in various directions. Some of the light travels back out of the cornea and to the wavefront sensor 1550. Measurements indicate that of the light sent into the cornea, only about 1/4000th is reflected back out. This light then travels as a semi-collimated beam back towards system 200.

Upon scattering, about 90% of the light retains its polarization. So the light traveling back towards system 200 is substantially still circularly polarized. The light then travels through aperture 1140 in principal surface 1120 of structure 1100, through quarterwave plate 1710, and is converted back to linear polarization. Quarterwave plate 1710 converts the polarization of the light from the eye's retina so that is it is P polarized, in contrast to probe beam received from third light source 1500 having the S polarization. This P polarized light then reflects off of first beamsplitter 1720, travels through telescope 1640, and then reaches polarizing beamsplitter 1620. Since the light is now P polarized relative the hypotenuse of polarizing beamsplitter 1620, the beam is transmitted and then continues onto wavefront sensor 1550.

When wavefront sensor 1550 is a Shack-Hartmann sensor, the light is collected by the lenslet array in wavefront sensor 1550 and an image of spots appears on the detector array (e.g., CCD) in wavefront sensor 1550. This image is then provided to processor 160 and analyzed to compute the refraction and aberrations of eye 10.

Although not shown in FIGS. 2-5, in some implementations optical measurement system 200 further includes one or more eye illumination sources and camera 120 for capturing images of a subject's eye 10.

Further details of various example implementations and operations of optical measurement system 200 may be found in U.S. Pat. No. 7,976,163, which is incorporated herein by reference.

As explained above, when making measurements of a subject's eye 10 it is desired to simultaneously insure that the subject's eye 10 should be drawn to its farthest possible refractive state by fixation target 1800, while also maintaining the pupil of eye 10 open with as large of a diameter as possible, and at least a diameter which is large enough to qualify the subject as a candidate for eye surgery (if such surgery is otherwise appropriate).

As further explained above, for older subjects fixation target 1800 should be maintained at a relatively dim level by decreasing the intensity of light source 1820 to open the pupil of eye 10. The present inventors have come to appreciate that a target brightness level of 0.5 cd/m$^2$ at eye 10 can produce good measurement results for many older subjects (e.g., subjects 43 years old and older).

On the other hand, the present inventors have come to appreciate that if fixation target 1800 has the dim brightness level (e.g., 0.5 cd/M$^2$) that is suitable for such older subjects, this brightness level is often not suitable for many younger subjects (e.g., subjects younger than 40 years old), because when a younger person views an object this dim, then the refractive state of the subject will frequently be accommodated. The present inventors have come to appreciate that it is only when a brighter target is moved into a fogged position, optically beyond the most accommodative state that a younger person's eye can achieve, that the eye reaches its farthest refractive state. In particular, the present inventors have come to appreciate that a target brightness level of 2.0 cd/m$^2$ at eye 10 can produce good measurement results for many younger subjects (e.g., subjects younger than 40 years old). Further, it has been found that at such a light level, the diameter of the pupil of such a younger person's eye will remain large enough to qualify the subject for eye surgery, such as LASIK.

Accordingly, beneficially optical measurement systems 100 and 200 execute one or more methods or algorithms for adjusting the brightness level of fixation target 1800, and particularly the intensity of light source 1820, according to a relevant characteristic of the subject whose eye 10 is being measured. An explanation of various embodiments of such methods and algorithms will be described now with respect to optical measurement system 100, but it should be understood that these descriptions also may be applied to optical measurement system 200.

In some embodiments, this method may include: providing a fixation target for a subject to view; determining or ascertaining the size or diameter of the subject's eye 10; and adjusting the brightness level of the fixation target to a selected brightness level corresponding to the ascertained diameter of the pupil of the eye 10. In some versions of these embodiments, a camera such as camera 120 may be used to ascertain the size or diameter of eye 10. For example, in some versions of these implementations an image of eye 10 may be displayed on display 150 and the operator may use an operator input device 180 (e.g., a roller ball, mouse, or touchscreen) to note on display 150 boundaries defining an extent of the pupil for ascertaining its diameter. In other versions, processor(s) 160 may execute a pattern recognition algorithm on an image of eye 10 produced by camera 120.

In some implementations, optical measurement system 100 automatically determines a selected brightness level for the fixation target based on the ascertained diameter of the pupil of eye 10. In some implementations, optical measurement system 100 may allow operator 20 to manually adjust the brightness level of the fixation target via an operator input device 180 in response to the detected pupil diameter.

In some implementations, processor(s) 150 of optical measurement system 100 provides an output signal to a light source of the fixation target which adjusts the intensity of the light source and thereby the brightness level of the fixation target to produce the selected brightness level.

In some embodiments, the method may include: receiving data pertaining to the subject; assigning the subject to an assigned age category based on the data pertaining to the subject; adjusting a brightness level of a fixation target to a selected brightness level corresponding to the assigned age category; and providing the fixation target for a subject to view. In various implementations, the data may include the subject's birth date, an age group or category to which the subject belongs, the subject's actual age, or any other information or data from which the subject may be assigned to a defined age category.

In some implementations, this data may be provided via on a data storage device or medium such as a FLASH card, optical disk, smart card, etc. In some implementations this data may be received from operator 20, via the user interface (e.g., operator input devices 180) of optical measurement system 100, for example as described below with respect to FIGS. 6A-6D.

In some embodiments, optical measurement system 100 processes the received data to assign the subject to one of two defined age categories based on an age threshold, and sets or adjusts the brightness level of the fixation target to a selected brightness level corresponding to the assigned age category while optical measurement system 100 measures one of more characteristics of the subject's eye 10. In some implementations, the age threshold is 43 years old. In that case, a subject may be assigned to either a first age category, less than 43 years old, or assigned to a second age category, 43 years old or older. However it should be understood that a different age threshold may be employed, for example 40 years old. When a subject is assigned to the first age category, then optical measurement system 100, and particularly processor(s) 160 of optical measurement system 100, sets or adjusts the fixation target to have a first intensity or brightness level, and when a subject is assigned to the second age category, then optical measurement system 100, and particularly processor(s) 160 of optical measurement system 100, sets or adjusts the fixation target to have a second intensity or brightness level which is less than the first intensity or brightness level. For example, the first brightness level may be about 0.5 cd/m$^2$, and the second brightness level may be about 2.0 cd/m$^2$. In other implementations, different brightness levels may be employed.

In some embodiments, optical measurement system 100 processes the received data to assign the subject to one of three defined age categories based on an two age thresholds, and sets or adjusts the brightness level of the fixation target to a selected brightness level corresponding to the assigned age category while optical measurement system 100 measures one of more characteristics of the subject's eye 10. In some implementations, the age thresholds are 30 years old and 43 years old. In that case, a subject may be assigned to either a first age category, under 30 years old, or assigned to a second age category, between 30 and 43 years old, or assigned to a third age category, 43 years old or older. However, it should be understood that different age thresholds may be employed. When a subject is assigned to the first age category, then optical measurement system 100, and particularly processor(s) 160 of optical measurement system 100, sets or adjusts the fixation target to have a first intensity or brightness level, when a subject is assigned to the second age category, then optical measurement system 100, and particularly processor(s) 160 of optical measurement system 100, sets or adjusts the fixation target to have a second intensity or brightness level which is less than the first intensity or brightness level, and when a subject is assigned to the third age category, then optical measurement system 100, and particularly processor(s) 160 of optical measurement system 100, sets or adjusts the fixation target to have a third intensity or brightness level which is less than the second intensity or brightness level.

In general, optical measurement system 100, and particularly processor(s) 160 of optical measurement system 100, may utilize any number of different age categories and may assign a subject to one of these age categories based on the received data pertaining to the subject. In some implementations, optical measurement system 100, and particularly processor(s) 160 of optical measurement system 100, may employ a look-up table or an equation to map the subject's age to a brightness level for the fixation target. For example, the brightness level of the fixation target may be gradually decreased with increasing age over some transition interval, say from 30 to 43 years or, or from 40 to 43 years old.

In some embodiments, optical measurement system 100 determines or ascertains one or more vision parameters of the subject, and adjusts the brightness level of the fixation target according to the determined vision parameter(s) for the subject while optical measurement system 100 measures one of more characteristics of the subject's eye 10. In some implementations, the vision parameter(s) may include a level of myopia of eye 10 and/or a level of astigmatism of eye 10. In some implementations, optical measurement system 100, and particularly processor(s) 160 of optical measurement system 100 may increase the brightness level of the fixation target when eye 10 exhibits strong myopia or strong astigmatism. In some implementations, optical measurement system 100 may ascertain the vision parameter(s) from data supplied to optical measurement system 100 by operator 20 via operator input device(s) 180. In other implementations, optical measurement system 100 may ascertain the vision parameter(s) from one or more initial measurements made by optical measurement system 100, for example by wavefront aberrometer 140. In some implementations, optical measurement system 100 may determine from hazy spots on a wavefront detector of wavefront aberrometer 140 that the subject's eye 10 has a cataract. In that case, optical measurement system 100, and particularly processor(s) 160 of optical measurement system 100 may increase the brightness level of the fixation target.

In some implementations, optical measurement system 100 may include a light detector or sensor which can sense an ambient level of level or a brightness level in the vicinity of optical measurement system 100. In that case, optical measurement system 100 may adjust one or all of the age-dependent brightness levels of fixation target depending on the ambient light level or brightness level. For example, if the level of ambient light is high (i.e., optical measurement system 100 is located in a bright room) then reducing the brightness level of the fixation target may have little or no effect in the diameter of the subject's pupil. In that case, the brightness level of the fixation target may be maintained at a higher level.

FIGS. 6A-6D illustrate several example embodiments of part of a user interface for an optical measurement system.

Figure 6A:
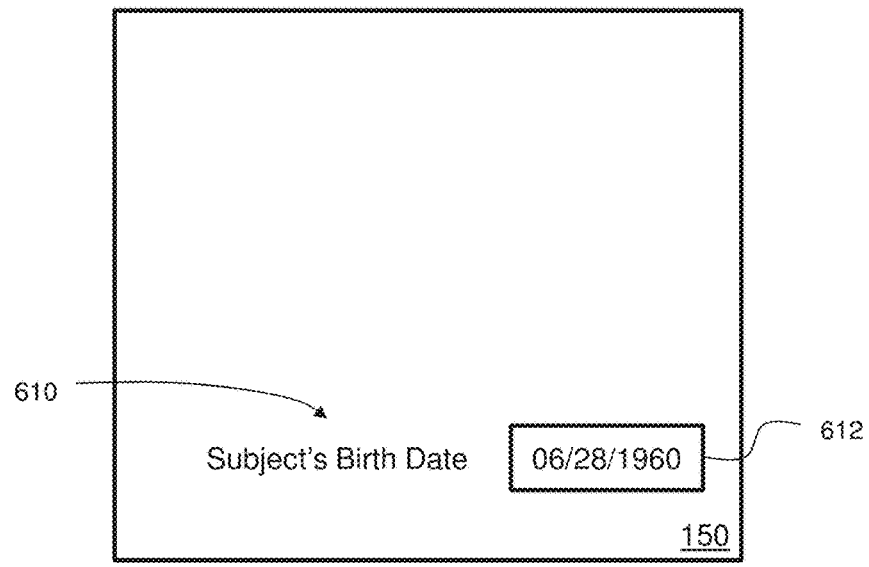
FIG. 6A, FIG. 6B, FIG. 6C and FIG. 6D illustrate embodiments of part of a user interface for an optical measurement system.

In FIG. 6A, optical measurement system 100 displays a message 310 to operator 20 via display 150 instructing or requesting the operator to enter the subject's birth date in a data entry box 312. In this case, if processor(s) 160 of optical measurement system 100 also have access to data which indicates the current date, then processor(s) 160 can determine the age of subject whose eye 10 is being measured.

Figure 6B:
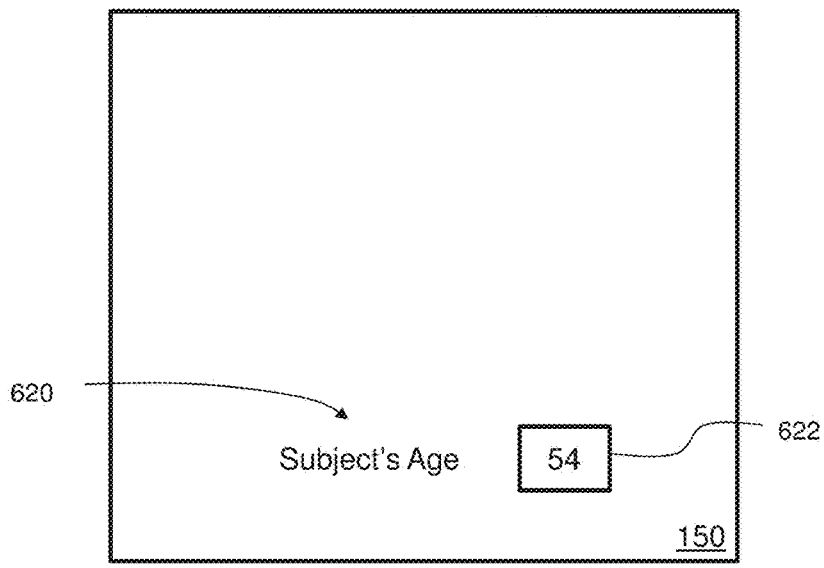

FIG. 6B illustrates a more direct way for optical measurement system 100, and more specifically processor(s) 160, to obtain data indicating the age of subject whose eye 10 is being measured. In this embodiment, optical measurement system 100 displays a message 320 to operator 20 via display 150 instructing or requesting the operator to enter the subject's age in a data entry box 322.

Figure 6C:
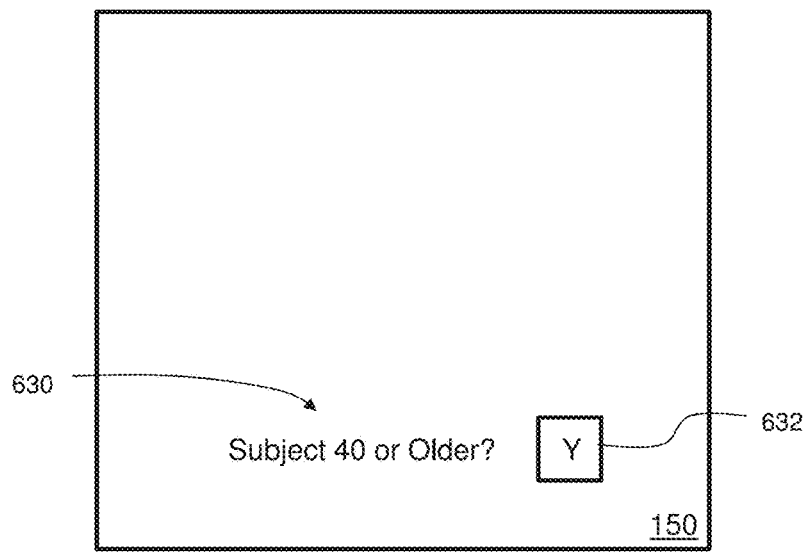
Figure 6D:
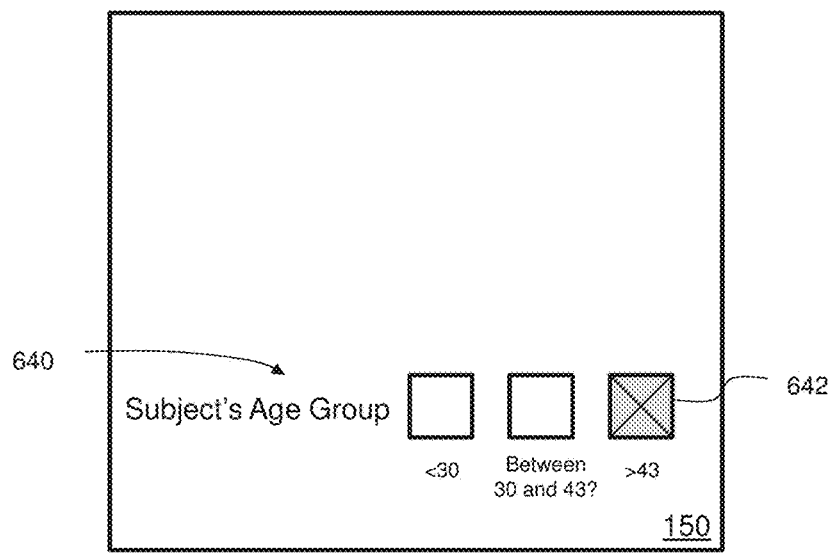

In the example embodiment of FIG. 6C, optical measurement system 100 displays an inquiry message 330 to operator 20 via display 150 asking the operator whether the subject is aged 40 or older. Operator 20 responds to the inquiry by entering a "Y" or "N" in data entry box 332.

In the example embodiment of FIG. 6C, optical measurement system 100 displays an inquiry message 330 to operator 20 via display 150 asking the operator whether the subject is aged 40 or older. Operator 20 responds to the inquiry by entering a "Y" or "N" in data entry box 332.

It should be understood that FIGS. 6A-D illustrate but a few examples of the many possible ways that optical measurement system 100 may receive data pertaining to the subject from which the subject may be assigned to a defined age category, as described above.

Figure 7:
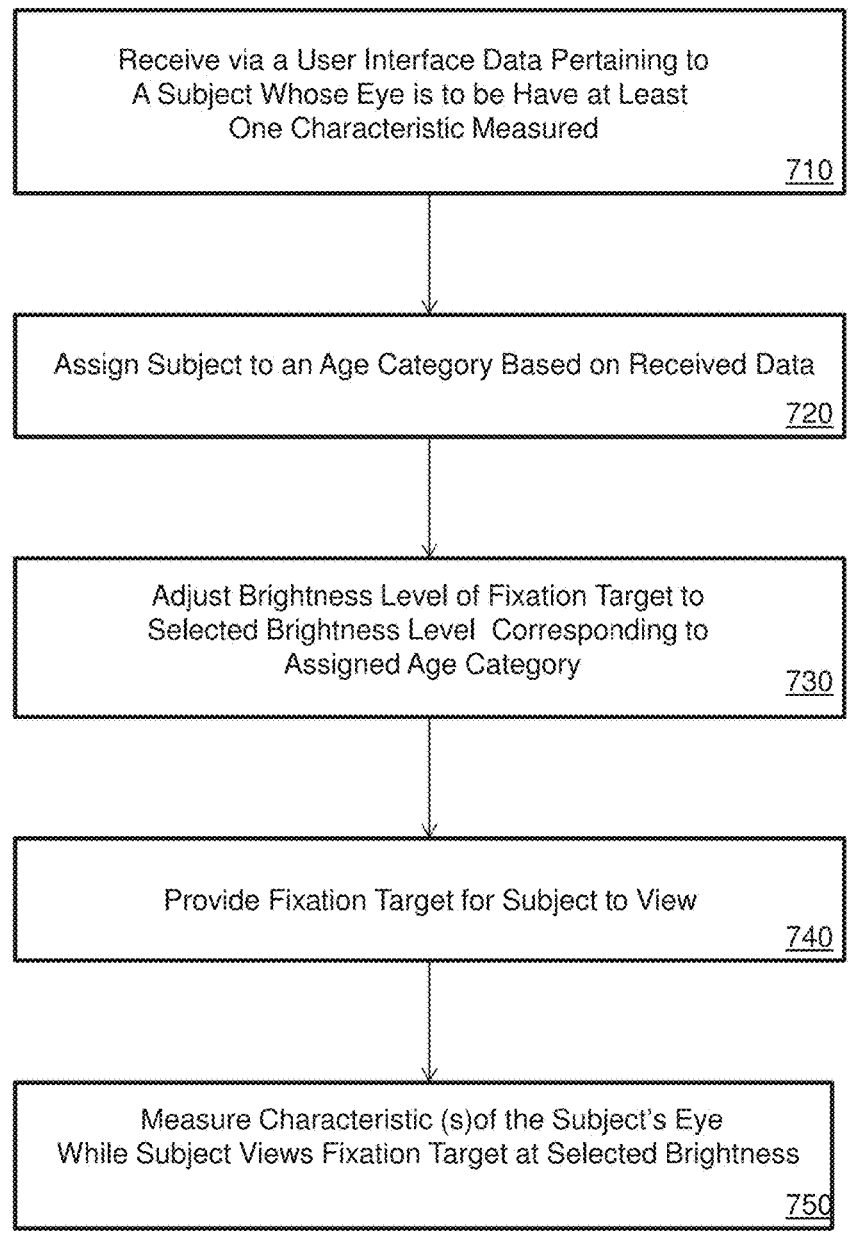
FIG. 7 illustrates a first example embodiment of a process of measuring a characteristic of a subject's eye with an appropriately lit fixation target.

FIG. 7 illustrates a first example embodiment of a process 700 of measuring a characteristic of a subject's eye with an appropriately lit fixation target. In some implementations, optical measurement systems 100 and/or 200 may employ process 700.

In an operation 710, an optical measurement system receives data pertaining to a subject whose eye is to have at least one characteristic measured by the optical measurement system. In some implementations, the data may comprise data received from an operator via one or more operator input devices as a user response to an inquiry presented to the operator by the optical measurement system via its user interface. In that case, in various implementations the user data may comprise any user data shown in FIGS. 6A-D as discussed above. In other implementations, the user data may be received stored on a data storage media, such as an optical disk, FLASH memory device; etc., which is interfaced to the optical measurement system.

In an operation 720, the optical measurement system assigns the subject to one of a plurality (e.g., 2 or 3) defined age categories based on the received data pertaining to the subject, as described above.

In an operation 730, the optical measurement system adjusts the brightness level of the fixation target to a selected brightness level corresponding to the assigned age category for the subject, as described above. In some implementations, a processor of the optical measurement system provides an output signal to a light source of the fixation target which adjusts the intensity of the light source and thereby the brightness level of the fixation target.

In an operation 740, the optical measurement system provides the fixation target for the subject to view. In some implementations, operation 740 may be performed before any one or all of the operations 710-730 so that the fixation target is displayed to the subject at some nominal intensity or brightness level, and then the intensity or brightness level is adjusted to the selected value corresponding to the assigned age category for the subject.

In an operation 750, the optical measurement system measures one or more characteristics of the subject's eye while the subject views the fixation target at the selected brightness level which corresponds to the assigned age category for the subject.

Figure 8:
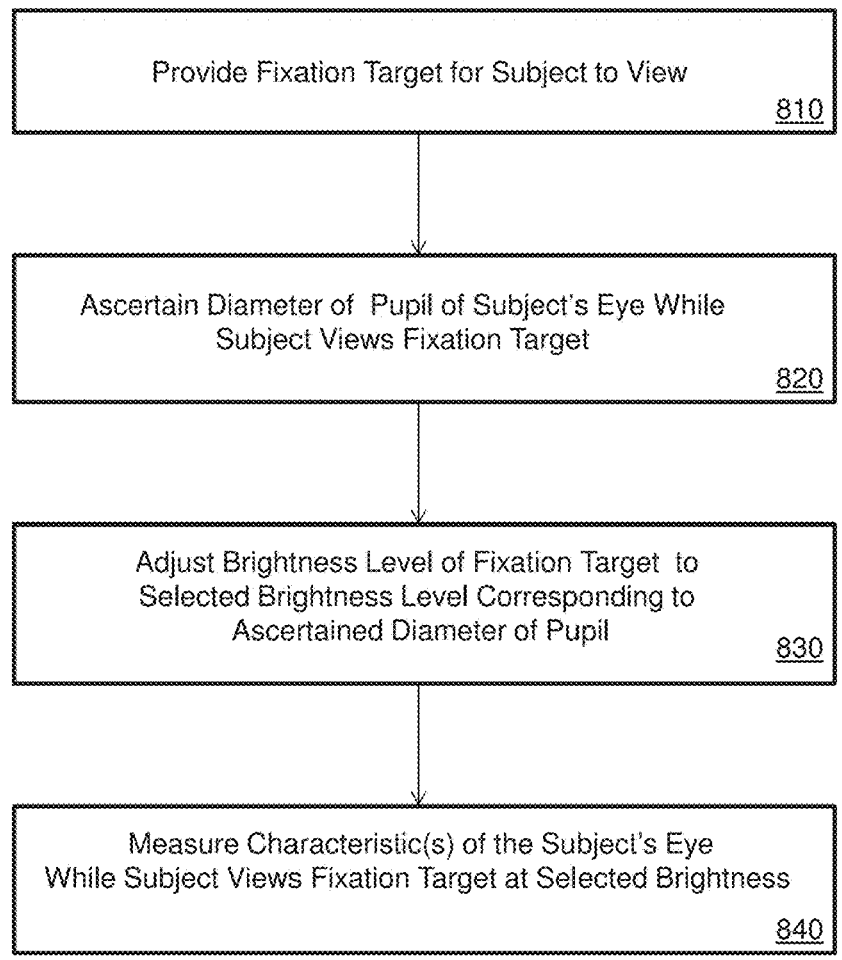
FIG. 8 illustrates a first example embodiment of a process of measuring a characteristic of a subject's eye with an appropriately lit fixation target.

FIG. 8 illustrates a first example embodiment of a process 800 of measuring a characteristic of a subject's eye with an appropriately lit fixation target.

In an operation 810, the optical measurement system provides a fixation target for the subject to view while optical measurements are made. In some implementations, the fixation target may be presented at a nominal brightness level which may be subsequently adjusted in operation 830 below. In other implementations, operations 820 and 830 may be performed before the fixation target is presented to the subject.

In an operation 820, the optical measurement system determines or ascertains the diameter of the pupil of the subject's eye, as described above.

In an operation 830, the optical measurement system adjusts the brightness level of the fixation target to a selected brightness level corresponding to the ascertained diameter of the pupil of the subject's eye, as described above. In some implementations, a processor of the optical measurement system provides an output signal to a light source of the fixation target which adjusts the intensity of the light source and thereby the brightness level of the fixation target.

In an operation 840, the optical measurement system measures one or more characteristics of the subject's eye while the subject views the fixation target at the selected brightness level which corresponds to the ascertained diameter of the pupil of the subject's eye.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Other variations are within the concept, scope, or spirit of the present invention. While the invention is susceptible to various modifications and alternative constructions, certain illustrated embodiments of the invention are shown in the drawings, and have been described above in an exemplary form with a certain degree of particularly. Those of ordinary skill in the art will understand, however, that the embodiments are provided by way of example only, and that various variations can be made without departing from the spirit or scope of the invention. Thus, there is no intention to limit the invention to the specific form or forms disclosed. Rather, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A method for measuring a characteristic of an eye of a subject, the method comprising:
providing a fixation target for a subject to view;
ascertaining a diameter of a pupil of the eye of the subject while the subject views the fixation target;
adjusting a brightness level of the fixation target to a selected brightness level corresponding to the ascertained diameter of the pupil of the eye; and
objectively measuring at least one characteristic of the eye of the subject while the subject views the fixation target at the selected brightness level.

2. The method of claim 1, further comprising:
detecting an ambient illumination level in a vicinity of an optical measurement system which objectively measures the at least one characteristic of the eye of the subject; and
adjusting the brightness level of the fixation target in response to the indicated ambient illumination level.

3. The method of claim 1, wherein ascertaining a diameter of a pupil of the eye of the subject while the subject views the fixation target comprises:
capturing an image of the eye;
displaying the image of the eye on a display; and
an operator using an operator input device to note on the display boundaries defining an extent of the pupil for ascertaining the diameter of the pupil.

4. The method of claim 1, wherein ascertaining a diameter of a pupil of the eye of the subject while the subject views the fixation target comprises:
capturing an image of the eye; and
performing pattern recognition on the image to identify the pupil and ascertain the diameter of the pupil.

5. The method of claim 1, wherein adjusting a brightness level of the fixation target to a selected brightness level comprises a processor providing an output signal to a light source of the fixation target which adjusts the intensity of the light source and thereby the brightness level of the fixation target.

6. The method of claim 1, wherein the optical measurement instrument is configured to measure at least one of a level of myopia of the eye and a level of astigmatism of the eye while the brightness level of the fixation target is adjusted according to the ascertained diameter of the eye.

7. The method of claim 1, wherein providing the fixation target for the subject to view includes:
disposing the fixation target on a movable stage; and
moving the movable stage to a position such that the eye can no longer focus on the fixation target to relax accommodation of the eye.

8. A system, comprising:
an optical measurement instrument configured for objectively measuring at least one characteristic of an eye of a subject;
a fixation target configured for a subject to view while the optical measurement instrument objectively measures the at least one characteristic of the eye; and
one or more processors, the one or more processors being configured to ascertain a diameter of a pupil of the eye of the subject, and to cause a brightness level of the fixation target to be adjusted according to the ascertained diameter of the eye while the optical measurement instrument objectively measures the at least one characteristic of the eye.

9. The system of claim 8, further comprising:
a detector configured for detecting an ambient illumination level in a vicinity of the system,
wherein the one or more processors is/are configured to adjust the brightness level of the fixation target in response to the indicated ambient illumination level.

10. The system of claim 8, wherein the optical measurement instrument comprises a wavefront aberrometer configured to measure ocular aberrations of the eye with the eye in its farthest possible refractive state from viewing the fixation target.

11. The system of claim 8, further comprising:
a camera configured to capture an image of the eye;
and a display configured to display the image of the eye; and
operator input device configured for an operator to note on the display boundaries defining an extent of the pupil for ascertaining the diameter of the pupil.

12. The system of claim 8, further comprising:
a camera configured to capture an image of the eye,
wherein the one or more processors are configured to perform pattern recognition on the image to identify the pupil and ascertain the diameter of the pupil.

13. The system of claim 8, further comprising a light source for illuminating the fixation target, wherein the one or more processors provide an output signal to the light source which adjusts the intensity of the light source and thereby the brightness level of the fixation target.

14. The system of claim 8, wherein objectively measuring at least one characteristic of the eye of the subject while the subject views the fixation target at the selected brightness level comprises measuring at least one of a level of myopia of the eye and a level of astigmatism of the eye.

15. The system of claim 8, wherein providing the fixation target for the subject to view includes:
disposing the fixation target on a movable stage; and
moving the movable stage to a position such that the eye can no longer focus on the fixation target to relax accommodation of the eye.

16. A method for measuring a characteristic of an eye of a subject, the method comprising:
providing a fixation target for a subject to view;
ascertaining a diameter of a pupil of the eye of the subject while the subject views the fixation target;
adjusting a brightness level of the fixation target to a selected brightness level corresponding to the ascertained diameter of the pupil of the eye; and
objectively measuring at least one characteristic of the eye of the subject while the subject views the fixation target at the selected brightness level,
wherein objectively measuring the at least one characteristic of the eye of the subject while the subject views the fixation target at the selected brightness level comprises measuring ocular aberrations of the eye with a wavefront aberrometer with the eye in its farthest possible refractive state from viewing the fixation target.

* * * * *